(12) United States Patent
Yu et al.

(10) Patent No.: US 6,436,688 B1
(45) Date of Patent: Aug. 20, 2002

(54) HUMAN LYSOZYME GENE, ITS ENCODING POLYPEPTIDE AND THE METHOD PREPARING FOR THEM

(75) Inventors: Long Yu; Qiang Fu; Yong Zhao; Honglai Zhang; Anding Bi, all of Shanghai (CN)

(73) Assignee: Institute of Genetics, Shanghai (CN)

( * ) Notice: Subject to any disclaimer, the term of this patent is extended or adjusted under 35 U.S.C. 154(b) by 0 days.

(21) Appl. No.: 09/786,023

(22) PCT Filed: Aug. 30, 1999

(86) PCT No.: PCT/CN99/00131

§ 371 (c)(1),
(2), (4) Date: Jun. 21, 2001

(87) PCT Pub. No.: WO00/12722

PCT Pub. Date: Mar. 9, 2000

(30) Foreign Application Priority Data

Aug. 31, 1998 (CN) .......................................... 98111039 A

(51) Int. Cl.[7] .............................. C12N 9/36; C07H 21/04
(52) U.S. Cl. .................. 435/206; 435/325; 435/252.33; 435/320.1; 536/23.2; 536/23.5
(58) Field of Search .............................. 435/206, 320.1, 435/252.33, 325; 536/23.2, 23.5

(56) References Cited

PUBLICATIONS

Hillier et al. Data Base: EST, Accession No.: AA416679, GI: 2077631 (Nov. 9. 1997).*
NCI–CGAP, Data Base: EST, Accession No.: AI066607, GI: 3367309 (Aug. 27, 1998).*

Online clipping from Entrez–PubMed, Dautigny et al., "cDNA and amino acid sequences of rainbow trout (*Oncorhynchus mykiss*) lysozymes and their implications for the evolution of lysozyme and lactalbumin", Dautigny et al. J. Mol Evol., vol. 32, issue 2, pp. 187–198, Feb. 1991.

Yajima et al. vol. 26, Issue 4 (1988). pp. 373–395. CRC Clinical Reviews in Food Science and Nutrition.

Mol Biol Evol Nov. 1994: 11(6) 921–8 Molecular adaptation of a leaf–eating bird: Stomach lysozyme of the hoatzin by Kornegay, Jr. et al.

J Biochem (Tokyo) Feb. 1982: 91 (2) 571–87 Chemical and immunlogical properties and amino acid sequences of three lysozymes from Peking—duck egg white; by Kondo et al.

Online clipping from Entrez–PubMed, Weisman et al., "Evolutionary shift in the site of cleavage of prelysome", J. Biol Chem, vol. 261, issue 5, pp. 2309–2313, 1986.

J Mol. Evol. Nov. 1991: 33(5) 418–25 "Stomach lysozyme gene of the langur monkey: tests for convergence and positive selection" by Swanson et al.

Nature 1997; Jan. 9: 385(6612) 151–4 "Episodic adaptive evolution of primate lysozymes" by Messier.

* cited by examiner

Primary Examiner—Nashaat T. Nashed
(74) Attorney, Agent, or Firm—Baker Botts LLP

(57) ABSTRACT

The invention relates to a novel member LYC2 of lysozyme gene family. The invention provides the cDNA sequence encoding for the novel lysozyme, the polypeptide encoded by the sequence, as well as the method for producing said novel human lysozyme utilizing recombinant technology. The invention also provides the use of the novel human lysozyme.

12 Claims, 2 Drawing Sheets

Figure 2A:
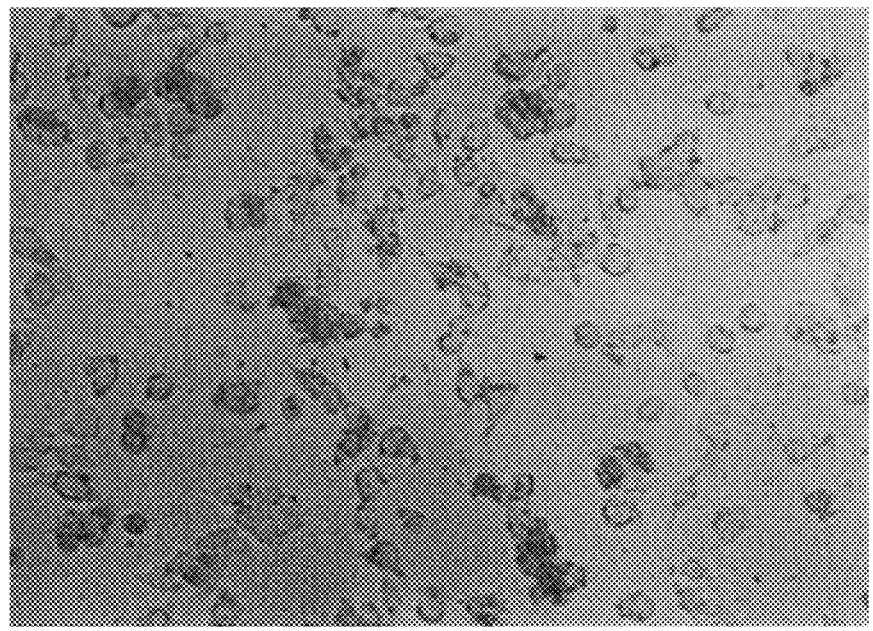

```
             10        20        30        40        50
LYC2     MKAAGILTLIGCLVT-GAESKIYTRCKLAKIFSRAGLDNYWGFSLGNWICMAYYESGYNT
         :..   .: :.  ...    .: .:.: ::.::   ..:  :::::  :.:::::.:  : .::..::
sp|00702 MRS--LLILVLCFLPLAAPGKVYGRCELAAAMKRMGLDNYRGYSLGNWVCAAKFESNFNT
              10        20        30        40        50

60        70        80        90        100       110
LYC2     TAQTVLDDGSIDYGIFQINTFAWCRRGKLK-ENNHCHVACSALITDDLTDAIICARKIVK
           :   .  :::  ::::.:::.    ::  :.       .:  ::.  ::::...:.:  ..  ::.:::.
sp|00702 GATNRNTDGSTDYGILQINSRWWCNDGRTPGSKNLCHIPCSALLSSDITASVNCAKKIVS
              60        70        80        90        100       110

120       130       140
LYC2     ETQGMNYWQGWKKHCEGRDLSEWKKGCEVS
          .  .:::  : ..:.:::.:  :..   : ..::..
sp|00702 DGNGMNAWVAWRKHCKGTDVNVWIRGCRL-
              120       130       140

Fig. 1A 10        20        30        40        50        60
LYC2     MKAAGILTLIGCLVTGAESKIYTRCKLAKIFSRAGLDNYWGFSLGNWICMAYYESGYNTT
         :::.  :: :.      ::  ...:.  ::.::.   ..:   :::.: :..:::.::..:  :  .:::::
sp|00702 MKAVIILGLVLLSVT-VQGKIFERCELARTLKRLGLDGYRGISLANWVCLAKWESGYNTQ
              10        20        30        40        50

70        80        90        100       110
LYC2     AQTVLD-DGSIDYGIFQINTFAWCRRGKLKEN-NHCHVACSALITDDLTDAIICARKIVK
           : .       : : ::::::::::.   ::   ::       :  :::..:.::   :...::.   :::..:.
sp|P30200 ATNYNPGDQSTDYGIFQINSHYWCNNGKTPGAVNACHISCNALLQDNIADAVTCAKRVVR
              60        70        80        90        100       110

120       130       140
LYC2     ETQGMNYWQGWKKHCEGRDLSEWKKGCEVS
          .  :::     :  :.:..:::..::.:.    .:: :
sp|P30200 DPQGIRAWVAWRNHCQNRDVSQYVQGCGV-
              120       130       140

Fig. 1B
```

HUMAN LYSOZYME GENE, ITS ENCODING POLYPEPTIDE AND THE METHOD PREPARING FOR THEM

FIELD OF THE INVENTION

The invention relates to a new polynucleotide, the polypeptide encoded by said polynucleotide, the uses of said polynucleotide and polypeptide, and the methods for preparing same. In particular, the invention relates to a new member of the lysozyme family.

PRIOR ART

Lysozyme exists ubiquitously in all parts of organisms, including various tissues, organs, and sera; it is especially abundant in egg white. Lysozyme is mainly secreted by the epithelial cell of certain glands and some kinds of leukocyte.

Lysozyme was first reported by Fleming, et al. in 1922. Afterward, lysozyme has been widely studied. A lot of papers concerning its crystal structure, protein catalytic domains, catalytic dynamics, immunology, molecular evolutionary, and so on, have been published. Lysozyme is one of the proteins that are studied most extensively and intensively. However, the study on lysozyme gene is not yet sufficient. Nowadays, only a few lysozyme genes from different species, such as E.coli T4, salmonella P22 phage, bacillus φ phage and chicken, etc., have been cloned. (1983 J. Mol. Biol. 165. 229–248; 1985 Virology 143, 280–289; 1987 Proc. Natl. Acad. Sci. USA, 77, 5759–5763). The cloning about human lysozyme gene was also reported (1988, Gene 66,223–234).

The main function of lysozyme is to hydrolyze the beta (1–4) glycosidic bond between N-acetylmuramic acid (NAM) and N-acetylgluconic acid (NAG) of the bacterial cell wall. In the organism, lysozyme can act as a nonspecific immune molecule against bacterial infections, and as a digestive enzyme in enteron and some mollusks which live on bacteria. Further, lysozyme has the function of inhibiting tumor growth. Therefore, lysozyme has important applications in both industry and medicine. One purpose of the invention is to provide a new polynucleotide which encodes a new member of lysozyme gene family. The new human lysozyme is named LYC2.

Another purpose of the invention is to provide a new member of lysozyme protein family, which is named LYC2.

Still another purpose of the invention is to provide a new method for preparing said new human lysozyme by recombinant techniques.

The invention also relates to the uses of said human lysozyme.

In one aspect, the invention provides an isolated DNA molecule, which comprises a nucleotide sequence encoding a polypeptide having human LYC2 protein activity, wherein said nucleotide sequence shares at least 70% homology to the nucleotide sequence of nucleotides 106–552 in SEQ ID NO: 3, or said nucleotide sequence can hybridize to the nucleotide sequence of nucleotides 106–552 in SEQ ID NO: 3 under moderate stringency. Preferably, said nucleotide sequence encodes a polypeptide comprising the amino acid sequence of SEQ ID NO: 4. More preferably, the sequence comprises the nucleotide sequence of nucleotides 106–552 in SEQ ID NO: 3.

Further, the invention provides an isolated LYC2 polypeptide, which comprises a polypeptide having the amino acid sequence of SEQ ID NO: 4, its active fragments, and its active derivatives. Preferably, the polypeptide is a polypeptide having the amino acid sequence of SEQ ID NO: 4.

The invention also provides a vector comprising said isolated DNA.

The invention further provides a host cell transformed with said vector.

In another aspect, the invention provides a method for producing a polypeptide with the activity of LYC2 protein, which comprises:

(a) forming an expression vector of LYC2 protein comprising the nucleotide sequence encoding the polypeptide having the activity of LYC2 protein, wherein said nucleotide sequence is operably linked with an expression regulatory sequences, and said nucleotide sequence shares at least 70% homology to the nucleotide sequence of positions 106–552 in SEQ ID NO: 3;

(b) introducing the vector of step (a) into a host cell, thereby forming a recombinant cell of LYC2 protein;

(c) culturing the recombinant cell of step (b) under the conditions suitable for the expression of LYC2 polypeptides;

(d) isolating the polypeptides having the activity of LYC2 protein.

In one embodiment of the present invention, the isolated polynucleotide has a full length of 610 nucleotides, whose detailed sequence is shown in SEQ ID NO: 3. The open reading frame (ORF) locates at nucleotides 106–552.

DETAILED DESCRIPTION

In the present invention, the term "isolated" or "purified" or "substantially pure" DNA refers to a DNA or fragment which has been isolated from the sequences which frank it in a naturally occurring state. The term also applied to DNA or DNA fragment which has been isolated from other components naturally accompanying the nucleic acid and from proteins naturally accompanying it in the cell.

In the present invention, the term "LYC2 protein encoding sequence" or "LYC2 polypeptide encoding sequence" refers to a nucleotide sequence encoding a polypeptide having the activity of LYC2 protein, such as the nucleotide sequence of positions 106–552 in SEQ ID NO: 3 or its degenerate sequence. The degenerate sequences refer to the sequences formed by replacing one or more codons in the ORF of 106–552 in SEQ ID NO: 3 with degenerate codes which encode the same amino acid. Because of the degeneracy of codon, the sequence having a homology as low as about 70% to the sequence of nucleotides 106–552 in SEQ ID NO: 3 can also encode the sequence shown in SEQ ID NO: 4. The term also refers to the nucleotide sequences that hybridize with the nucleotide sequence of nucleotides 106–552 in SEQ ID NO: 3 under moderate stringency or preferably under high stringency. In addition, the term also refers to the sequences having a homology at least 70%, preferably 80%, more preferably 90% to the nucleotide sequence of nucleotides 106–552 in SEQ ID NO: 3.

The term also refers to variants of the sequence in SEQ ID NO: 3, which are capable of coding for a protein having the same function as human LYC2 protein. These variants includes, but are not limited to: deletions, insertions and/or substitutions of several nucleotides (typically 1–90, preferably 1–60, more preferably 1–20, and most preferably 1–10) and additions of several nucleotides (typically less than 60, preferably 30, more preferably 10, most preferably 5) at 5' end and/or 3' end.

In the present invention, "substantially pure" proteins or polypeptides refers to those which occupy at least 20%, preferably at least 50%, more preferably at least 80%, most preferably at least 90% of the total sample material (by wet weight or dry weight). Purity can be measured by any appropriate method, e.g., in the case of polypeptides by column chromatography, PAGE or HPLC analysis. A substantially purified polypeptides is essentially free of naturally associated components.

In the present invention, the term "LYC2 polypeptide" or "LYC2 protein" refers to a polypeptide having the activity of LYC2 protein comprising the amino acid sequence of SEQ ID NO: 4. The term also comprises the variants of said amino acid sequence which have the same function of human lysozyme. These variants include, but are not limited to, deletions, insertions and/or substitutions of several amino acids (typically 1–50, preferably 1–30, more preferably 1–20, most preferably 1–10), and addition of one or more amino acids (typically less than 20, preferably less than 10, more preferably less than 5) at C-terminal and/or N-terminal. For example, the protein function are usually unchanged when an amino residue is substituted by a similar or analogous one. Further, the addition of one or several amino acids at C-terminal and/or N-terminal will not change the function of protein. The term also includes the active fragments and derivatives of LYC2 protein.

The variants of polypeptide include homologous sequences, allelic variants, natural mutants, induced mutants, proteins encoded by DNA which hybridizes to LYC2 DNA under high or low stringency conditions as well as the polypeptides or proteins retrieved by antisera raised against LYC2 polypeptide. The present invention also provides other polypeptides, e.g., fusion proteins, which include the LYC2 polypeptide or fragments thereof. In addition to substantially full-length polypeptide, the soluble fragments of LYC2 polypeptide are also provided. Generally, these fragments comprise at least 10, typically at least 30, preferably at least 50, more preferably at least 80, most preferably at least 100 consecutive amino acids of human LYC2 polypeptide.

The present invention also provides the analogues of LYC2 protein or polypeptide. Analogues can differ from naturally occurring LYC2 polypeptide by amino acid sequence differences or by modifications which do not affect the sequence, or by both. These polypeptides include genetic variants, both natural and induced. Induced variants can be made by various techniques, e.g., by random mutagenesis using irradiation or exposure to mutagens, or by site-directed mutagenesis or other known molecular biologic techniques. Also included are analogues which include residues other than those naturally occurring L-amino acids ( e.g., D-amino acids) or non-naturally occurring or synthetic amino acids (e.g., beta- or gamma-amino acids). It is understood that the polypeptides of the invention are not limited to the representative polypeptides listed hereinabove.

Modifications ( which do not normally alter primary sequence) include in vivo, or in vitro chemical derivation of polypeptides, e.g., acelylation, or carboxylation. Also included are modifications of glycosylation, e.g., those made by modifying the glycosylation patterns of a polypeptide during its synthesis and processing or in the further processing steps, e.g., by exposing the polypeptide to enzymes which affect glycosylation (e.g., mammalian glycosylating or deglycosylating enzymes). Also included are sequences which have phosphorylated amino acid residues, e.g., phosphotyrosine, phosphoserine, phosphothronine, as well as sequences which have been modified to improve their resistance to proteolytic degradation or to optimize solubility properties.

The invention also includes antisense sequence of the sequence encoding LYC2 polypeptide. Said antisense sequence can be used to inhibit expression of LYC2 in cells.

The invention also include probes, typically having 8–100, preferably 15–50 consecutive nucleotides. These probes can be used to detect the presence of nucleic acid molecules coding for LYC2 in samples.

The present invention also includes methods for detecting LYC2 nucleotide sequences, which comprises hybridizing said probes to samples, and detecting the binding of the probes. Preferably, the samples are products of PCR amplification. The primers in PCR amplification correspond to coding sequence of LYC2 polypeptide and are located at both ends or in the middle of the coding sequence. In general, the length of the primers is 20 to 50 nucleotides.

A variety of vectors known in the art, such as those commercially available, are useful in the invention.

In the invention, the term "host cells" includes prokaryotic and eukaryotic cells. The common prokaryotic host cells include Escherichi coli, Bacillus subtilis, and so on. The common eukaryotic host cells include yeast cells, insect cells, and mammalian cells. Preferably, the host cells are eukaryotic cells, e.g., CHO cells, COS cells, and the like.

In another aspect, the invention also includes antibodies, preferably monoclonal antibodies, which are specific for polypeptides encoded by LYC2 DNA or fragments thereof. By "specificity" is meant an antibody which binds to the LYC2 gene products or a fragments thereof. Preferably, the antibody binds to the LYC2 gene products or a fragments thereof and does not substantially recognize and bind to other antigenically unrelated molecules. Antibodies which bind to LYC2 and block LYC2 protein and those which do not affect the LYC2 function are included in the invention. The invention also includes antibodies which bind to the LYC2 gene product in its unmodified as well as modified form.

The present invention includes not only intact monoclonal or polyclonal antibodies, but also immunologically-active antibody fragments, e.g., a Fab' or (Fab)$_2$ fragment, an antibody light chain, an antibody heavy chain, a genetically engineered single chain Fv molecule (Lander, et al., U.S. Pat. No. 4,946,778), or a chimeric antibody, e.g., an antibody which contains the binding specificity of a murine antibody, but the remaining portion of which is of human origin.

The antibodies in the present invention can be prepared by various techniques known to those skilled in the art. For example, purified LYC2 gene products, or its antigenic fragments can be administrated to animals to induce the production of polyclonal antibodies. Similarly, cells expressing LYC2 or its antigenic fragments can be used to immunize animals to produce antibodies. Antibodies of the invention can be monoclonal antibodies which can be prepared by using hybridoma technique (See Kohler, et al., Nature, 256; 495,1975; Kohler, et al., Eur. J. Immunol. 6: 511,1976; Kohler, et al., Eur. J. Immunol. 6: 292, 1976; Hammerling, et al., In Monoclonal Antibodies and T Cell Hybridomas, Elsevier, N.Y., 1981). Antibodies of the invention comprise those which block LYC2 function and those which do not affect LYC2 function. Antibodies in the invention can be produced by routine immunology techniques and using fragments or functional regions of LYC2 gene product. These fragments and functional regions can be prepared by recombinant methods or synthesized by a polypeptide synthesizer. Antibodies binding to unmodified LYC2 gene product can be produced by immunizing animals with gene products produced by prokaryotic cells (e.g., E.

coli); antibodies binding to post-translationally modified forms thereof can be acquired by immunizing animals with gene products produced by eukaryotic cells (e.g., yeast or insect cells).

In one embodiment, the polynucleotide of the invention is 610 bp in fall length whose detailed sequence is shown in SEQ ID NO: 3 with the ORF located at positions 106–552. Said polynucleotide was obtained as follows: human brain λ gt 11 cDNA library (Clontech) was used as a template and PCR was carried out with the synthetic forward primer A1: 5'-ACTAGGTGTATCAGTGTTTCTTC-3' (SEQ ID NO:1) and reverse primer B:5'-GGACATTCACTGCAAATCCTAGG-3'(SEQ ID NO:2). A target fragment of 610 bp was obtained. The sequencing of the PCR product gave the full length cDNA sequence shown in SEQ ID NO: 3.

Homology comparison showed that the nucleotide sequence and the coded protein sequence of the invention shared remarkable homology to other lysozymes from different origins. Therefore, it indicates it is a new member of lysozyme family and has some important functions of the family.

Lysozyme can lyse cells by hydrolyze the beta(1–4) glycosidic bond between N-acetylmuramic acid (NAM) and N-acetylgluconic acid (NAG) of the bacterial cell wall. In the organisms, lysozyme can act as a nonspecific immune molecule against bacterial infections, and as a digestive enzyme in enteron and some mollusks which live on bacteria. Further, lysozyme has the function of inhibiting tumor growth. In 1955, Caselli and Shumacher (Boll Ocul 34:513–533, 1955) reported on the lysozyme-mediated 70% inhibition of neoplastic transformation in cornea of chicken infected by Rous sarcoma virus. Many other experiments indicated that lysozyme participates in the process of tumor diffusion and interacts with phospho- and glucolipid molecule of tumor cells. The inhibition effect on human tumor of lysozyme was reported and patented (1980 Jpn Kokai, Tokkyo Koho 33,409; 1980 Jpn Kokai Tokkyo Koho 33,408). As to the mechanism of lysozyine inhibition on tumor, there are two possibilities: (1) lysozyme directly activates the organism's immunity functions; (2) lysozyme indirectly enhances the organism's immune ability (1989 Anticancer Research 9, 583–592).

FIGURE DESCRIPTION

FIGS. 1A and 1B shows an alignment of amino acid sequence of human LYC2 with lysozyme C of ringnecked pheasant (sp/p00702) and lysozyme C of red guenon (sp/p30200), respectively. Identical amino acid are indicated by ":", and similar amino acids are indicated by ".". Similar amino acids are A, S, and T; and E; N and Q; R and K; I, L, M and V; and F, Y and W.

Figure 2B:
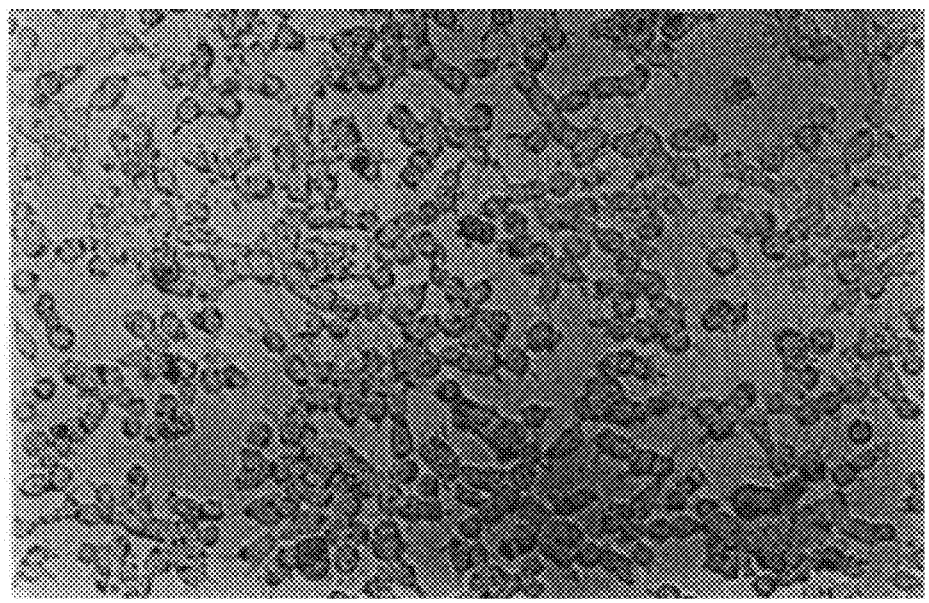

FIGS. 2A and 2B show the cytolysis of cancer cells by human LYC2. FIG. A shows the nasopharyngeal carcinoma cells treated for 24 h with the supernatant of CHO cell transformed with pcDNA3-LyC2. FIG. 2B shows the nasopharyngeal carcinoma cells treated for 24 h with the supernatant of CHO cell transformed with control vector pcDNA3.

The invention is further illustrated by the following examples. It is appreciated that these examples are only intended to illustrate the invention, but not to limit the scope of the invention. For the experimental methods in the following examples, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified.

EXAMPLE 1

The Cloning and Sequencing of LYC2 cDNA Sequence

1. Amplification with Primers

The template was human brain λ gt 11 cDNA library (commercially available from Clontech). PCR with forward primer A1: 5'-ACTAGGTGTATCAGTGTTTCTTC-3' (SEQ ID NO: 1) and reverse primer B :5'-GGACATTCACTGCAAATCCTAGG-3' (SEQ ID NO: 2) was carried out. The PCR condition for A1/B was 4 mins at 93° C.; followed by 35 cycles with 1 min at 93° C., 1 min at 64° C., and 1 min at 72° C.; and, finally 5 mins at 72° C. The PCR fragments were detected by electrophoresis. The target fragment was 610 bp.

2. Sequencing PCR Products

The obtained PCR products were linked with pGEM-T® vector (Promega) and transformed into E. coli JM103. The plasmids were extracted using QIAprep Plasmid Kit (QIAGEN). The oriented serial deletion of the inserted fragments was carried out with Double-Stranded Nested Deletion Kit (Pharmacia), and the deletants were quickly identified by PCR and arranged in order. The deletants successively cut-off were sequenced with SequiTherm EXCEL™ DNA Sequencing Kit (Epicentre Technologies). A full length cDNA sequence of 610 bp was obtained by overlapping the sequences with computer software. The detailed sequence is shown in SEQ ID NO: 3 with an open reading frame (ORF) located at nucleotides 106–552.

According to the resultant full-length cDNA sequence, the amino acid sequence of LYC2 was deduced, having 148 amino acid residues totally. See SEQ ID NO: 4 for its amino acid sequence in details.

EXAMPLE 2

Homologous Comparison

The full length cDNA sequence of LYC2 and the coded protein were used for homologous screening Non-redundant GenBank+EMBL+DDBJ+PDB and GenBank CDS translations+PDB+SwissProt+Spupdate+PIR databases by BLAST algorithm. The result showed that they shared high homology to other members of the lysozyme family. The amino acid sequence of LYC2 shares 46.7% identity and 64% similarity with ring-necked pheasant's lysozyme C (sp|p00702), and 45.3% identity and 60% similarity with lysozyme C of red guenon (sp|p30200), when analyzed by PCGENE software.

In particular, in amino acid sequence of LYC2, there exists a 19 amino acids signature sequence of lysozyme and alpha-lactoalbumin: $CX_3CX_2(L/M/F)X_3(D/E/N)(L/I)X_5C$ [Note: In the sequence, X represents any amino acid, digits such as "2" denote the number of amino acid, "(L/M/H)" represents any of these three amino acids]. Lysozyme and alpha-lactoalbumin are two proteins related closely in evolution (Eur. J. Biochem. 182: 111–118). In the protein of the present invention, the sequence matching the signature is: CHVACSALITDDLTDAIIC (residues 94–112 in SEQ ID NO: 4). It indicates that the LYC2 of the present invention belongs to lysozyme family, and has the relative functions of the lysozyme family.

Lysozyme can lyse cells by hydrolyze the beta(1–4) glycosidic bond between N-acetylmuramic acid (NAM) and N-acetylgluconic acid (NAG) of the bacterial cell wall. In the organisms, lysozyme can act as a nonspecific immune molecule against bacterial infections, and as a digestive enzyme in enteron and some mollusks which live on bacteria.

Lysozyme has important applications in both industry and medicine.

First, in industry (mainly in food industry), lysozyme can be used as a preservative or additive for food. In this respect, the Japanese have developed many use of lysozyme and owe many patents. For example, they use lysozyme as a preservative for fresh fruit, vegetable, soybean milk, marine foods and meat. Lysozyme can also be used as an additive for infant's foods to simulate human milk (1988, Crit Rev Food Sci Nutr 26(4):359–395).

In respect of pharmaceutical use, lysozyme can be used to cure viral and bacterial infections. For example, EDTA-tris-lysozyme solutions are effective on the pseudomonas cystitis induced by E.coli infection. Lysozyme concentration in human and animal serum is an indicator of infection. Zajaczkowska-Bialowas and Murai studied the relationship between lysozyme activity in saliva and diseases of oral cavity. The result showed that lysozyme had obvious alleviation effect on the symptom of chronic periodontitis. Besides, they found the synergistic effects of lysozyme and some antibiotics. When lysozyme was used alone, even in a large amount, the bacteriolysis effect on S. aureus was little. But with the presence of amoxicillin, the lysis effect was enhanced and in proportion to the amount of lysozyme (1988 Crit Rev Food Sci Nutr 26(4):359–395).

Further, lysozyme has the function of inhibiting tumor growth. In 1955, Caselli and Shumacher (1955, Boll Ocul 34:513–533) reported on the lysozyme-mediated 70% inhibition of neoplastic transformation in cornea of chicken infected by Rous sarcoma virus. Many other experiments indicated that lysozyme had some relationship to the inhibition of tumor diffusion (1988 Clin. Expl. Metastasis 6:245–253; 1998 Folia Onclo 10, Suppl A: 219–224; 1988 Eur. J. Cancer Clin. Onco. 124:1737–1743). It is also found that lysozyme interacts with phospho- and glucolipid molecule of tumor cells. The lysozyme's inhibition effect on human tumor was reported. Laterza successfully cured a case of small intestine reticulation sarcoma with diffusion after operation and radiotherapy ("Atti del II Simposium Internazionale sul Lisozima", Milano. 7–8–9 1961. Vol I, sez V, pp 49–50). Battaglia et al. found that, though lysozyme could not reduce the volume of tumor, it had distinct effects of pain-killing and helping recovery in curing carcinomas of stomach, prostate, uterus and mammary gland ("Atti del II Simposium Internaionale sul Lisozima di Fleming", Milano. 3–4–5 1964. Vol I, sez IV, pp 69–76). In Japan, the application of lysozyme in curing cancer was patented (1980 Jpn Kokai Tokkyo Koho 33, 409; 1980 Jpn Kokai Tokkyo Koho 33,408). Besides, A. Vacca et al. in 1985 reported an attempt of curing multiple myeloma by chemoimmunology with oral lysozyme as an immunomodulating agent. Their experiments indicated that 50% of the patients treated with a large amount of lysozyme had improved immune ability as compared with the controls (Chemiother IV n.2:147–155,1985). As to the mechanism of lysozyme inhibition on tumor, there are two possibilities: (1) lysozyme directly activates the organism's immunity functions; (2) lysozyme indirectly enhances the organism's immune ability (1989 Anticancer Research 9, 583–592).

EXAMPLE 3

Expression of LYC2 in E. coli

The cDNA sequence encoding LYC2 was amplified with oligonucleotide PCR primers corresponding to 5'- and 3'-end of said DNA sequence, using human brain λ gt 11 cDNA library (Clontech) as a template. The resultant product was used as an insertion fragment.

The sequence of 5'-end oligonucleotide primer was:

5'-TTCCGGATCCATGAAGGCTGCGGGCATTC-3' (SEQ ID NO: 5).

This primer contained a cleavage site of restriction endonuclease BamH I, followed by 19 nucleotides of LYC2 coding sequence starting from the start codon.

The sequence of 3'-end primer was:

5'-CTTCGTCGACTTAGGAAACCTCACAGCCT-3' (SEQ ID NO: 6).

This primer contains a cleavage site of restriction endonuclease SalI, a translation terminator and partial LYC2 coding sequence.

These cleavage sites of restriction endonuclease in primers corresponded to the cleavage sites in bacterial expression vector pQE-9 (Qiagen Inc., Chatsworth, Calif.). Vector pQE-9 encodes an antibiotic resistance (Amp'), a bacterial replication origin (ori), an IPTG-adjustable promotor/operon (P/O), a ribosome-binding site (RBS), a six-hisitine tag (6-His) and cloning sites of restriction endonuclease.

Vector pQE-9 and insertion fragments were digested by BamHI and SalI, and then linked together, ensuring that the open reading frame started from the bacterial RBS. Then, the linkage mixture was used to transform E.coli M15/rep4 (Qiagen) containing multi-copy of plasmid pREP4 which expressed repressor of lacI and was resistant to kanamycin (Kan'). Transformants were screened out in LB medium containing Amp and Kan. The positive clones of transformant were cultured overnight in LB liquid medium supplemented with Amp (100 ug/ml) and Kan (25 ug/ml). The plasmids were extracted. The size and direction of the inserted fragments were verified by HindIII digestion. The sequencing confirmed that LYC2 cDNA fragment was correctly inserted into the vector.

The overnight culture was 1:100–1:250 diluted, inoculated into large volume medium, and cultured until the 600 nm optical density ($OD_{600}$) reached 0.4–0.6. IPTG (isopropylthio-beta-D-galactoside) was added to final concentration of 1 mM. By deactivating repressor of LacI, IPTG induced and promoted P/O, thereby increasing the expression of gene. The cells were cultured for another 3–4 hours, and then centrifuged (6000 Xg, 20 mins). The inclusions were sonicated, and cell was collected and precipitates was solved in 6M guanidine hydrochloride. After clarification, the dissolved LYC2 in solution were purified by nickel-chelated column chromatography under the conditions suitable for the tight binding of 6-His tagged protein and column. LYC2 was eluted with 6M-guanidine hydrochloride (pH 5.0). The denaturalized proteins in guanidine hydrochloride were precipitated by several methods. First, guanidine hydrochloride was separated by dialysis. Alternatively, the purified protein, which was isolated from nickel-chelated column, bound to the second column with decreased linear gradient of guanidine hydrochloride. The proteins were denatured when binding to the column, and then eluted with guanidine hydrochloride (pH 5.0). Finally, the soluble proteins were dialyzed with PBS, then preserved in glycerol stock solution with the final glycerol concentration of 10% (w/v).

The molecular weight of the expressed protein was about 17 kDa, as identified by 12% SDS-PAGE.

Moreover, the sequencing results of the 10 amino acids at the N- and C-terminal of the expressed protein indicated that they were identical to those in SEQ ID NO: 4.

EXAMPLE 4

Expression of LYC2 in Eukaryotic Cells (CHO cell line)

In this example, the cDNA sequence encoding LYC2 was amplified with oligonucleotide PCR primers corresponding to 5'- and 3'-end of said DNA sequence, using human brain λ gt 11 cDNA library (Clontech) as a template. The resultant product was used as an insertion fragment.

The sequence of 5'-end oligonucleotide primer was:

5'-TCCAAGCTTATGAAGGCTGCGGGCATTC-3'(SEQ ID NO: 7),

This primer contained a cleavage site of restriction endonuclease HindIII, followed by 20 nucleotides of LYC2 coding sequence starting from the start codon.

The sequence of 3'-end primer was:

5'-CTTCGGATCCTTAGGAAACCTCACAGCCT-3' (SEQ ID NO: 8)

The primer contained a cleavage site of restriction endonuclease BamHI, a translation stop codon, and partial LYC2 coding sequence.

These cleavage sites of restriction endonuclease in primers corresponded to the cleavage sites in expression vector pcDNA3 for CHO cell. This vector encoded two kinds of antibiotic resistance (Amp$^r$ and Neo$^r$), a phage replication origin (fl ori), a virus replication origin (SV40 ori), a T7 promoter, a virus promoter (P-CMV), a Sp6 promoter, a polyadenylation signal of SV40 and the corresponding polyA sequence thereof, a polyadenylation signal of BGH and the poly A sequence thereof.

The vector pcDNA3 and insertion fragment were digested with HindIII and BamHI, and linked together. Subsequently, E.coli strand DH5 α was transformed with linkage mixture. Transformants were screened out in LB medium containing Amp. The clones containing the needed constructs were cultured overnight in LB liquid medium supplemented with Amp (100 ug/ml). Plasmids were extracted. The sequencing indicated that LYC2 cDNA fragment was correctly inserted into the vector.

Plasmids were transfected into CHO cells by lipofection with Lipofectin Kit (GIBco Life). After transfecting the cells for 48 hours and screening the cells with G418 for 2–3 weeks, the cells and cell supernatant were collected and the enzyme activity of the expressed protein was measured. G418 was removed and the transformants were subcultured continuously. The mixed clonal cells were limiting diluted and the subclones with higher protein activity were selected. The positive subclones were mass cultured by routine methods. 48 hours later, the cells and supernatant were collected. The cells were ultrasonicated. Using 50 mM Tris-HCl (pH7.6) solution containing 0.05% Triton as an equilibrium solution and eluent, the active peek of the protein was collected with a pre-balanced Superdex G-75 column. Then, using 50 mM Tris-HCl (pH8.0) solution containing 0–1 M NaCl as an eluent, the protein was gradiently washed on a DEAE-Sepharose column balanced with 50 mM Tris-HCl (pH 8.0) solution. The active peek of the protein was collected. The solution of the expressed protein was dialyzed with PBS (pH 7.4), and finally lyophilized and preserved.

The molecular weight of the expressed protein was 17 kDa as identified by 12% SDS-PAGE.

Moreover, the sequencing results of the 10 amino acids at the N- and C-terminal of the expressed protein indicated that they were identical to those in SEQ ID NO: 4.

EXAMPLE 5

Antibody Preparation

Antibodies were produced by immunizing animals with the recombinant proteins obtained in the above examples. The method was as follows: the recombinant proteins were isolated by chromatography, and stored for use. Alternatively, the protein was isolated by SDS-PAGE electrophoresis, and obtained by cutting eletrophoretic bands from gel. The protein was emulsified with Freund's complete adjuvant of the same volume. The emulsified protein was injected intraperitoneally into mice at a dosage of 50–100 ug/0.2 ml. 14 days later, the same antigen was emulsified with Freund's incomplete adjuvant and injected intraperitoneally into mice at a dosage of 50–100 ug/0.2 ml for booster immunization. Booster immunization was carried out every 14 days, for at least three times. The specific activity of the obtained antiserum was evaluated by its ability of precipitating the translation product of LYC2 gene in vitro.

All the documents cited herein are incorporated into the invention as reference, as if each of them is individually incorporated. Further, it is appreciated that, in the above teaching of the invention, the skilled in the art can make certain changes or modifications to the invention, and these equivalents are still within the scope of the invention defined by the appended claims of the present application.

What is claimed is:

1. An isolated DNA molecule having a nucleotide sequence encoding a polypeptide having the amino acid sequence of SEQ ID NO:4 or amino acids 20–148 of SEQ ID NO:4.

2. The DNA molecule of claim 1 wherein said nucleotide sequence encodes a polypeptide having the amino acid sequence of amino acids 20–148 of SEQ ID NO: 4.

3. The DNA molecule of claim 1 wherein said nucleotide sequence has the nucleotide sequence of nucleotides 106–552 of SEQ ID NO: 3.

4. An isolated LYC2 polypeptide having the amino acid sequence of SEQ ID NO: 4 or of amino acids 20–148 of SEQ ID NO: 4.

5. The polypeptide of claim 4 wherein said polypeptide has the amino acid sequence of amino acids 20–148 of SEQ ID NO: 4.

6. A vector containing the DNA sequence of claim 1.

7. A host cell transformed by the vector of claim 6.

8. The host cell of claim 7 which is *E.coli.*

9. The host cell of claim 7 which is a eukaryotic cell.

10. A method for producing a LYC2 protein which comprises:
    (a) introducing an expression vector for producing a LYC2 protein, said vector comprising a nucleotide sequence encoding a polypeptide having the amino acid sequence of SEQ ID NO:4 or of amino acids 20–148 of SEQ ID NO:4, wherein said nucleotide sequence is operably linked to at least one expression control sequence, into a host cell, thereby forming a recombinant host cell;
    (b) culturing the recombinant host cell of (a) under conditions suitable for expression of the DNA molecule encoding the polypeptide, such that LYC2 protein is produced; and
    (c) isolating the LYC2 protein so produced.

11. The method of claim 10 wherein said nucleotide sequence comprises nucleotides 106–552 of SEQ ID NO: 3.

12. An isolated nucleotide molecule which is the antisense sequence of the DNA molecule of claim 1.

* * * * *

SEQUENCE LISTING

```
<160> NUMBER OF SEQ ID NOS: 12

<210> SEQ ID NO 1
<211> LENGTH: 23
<212> TYPE: DNA
<213> ORGANISM: Human
<220> FEATURE:
<223> OTHER INFORMATION: Oligonucleotide primer

<400> SEQUENCE: 1
actaggtgta tcagtgtttc ttc                                          23

<210> SEQ ID NO 2
<211> LENGTH: 23
<212> TYPE: DNA
<213> ORGANISM: Human
<220> FEATURE:
<223> OTHER INFORMATION: Oligonucleotide primer

<400> SEQUENCE: 2
```

```
ggacattcac tgcaaatcct agg                                              23

<210> SEQ ID NO 3
<211> LENGTH: 610
<212> TYPE: DNA
<213> ORGANISM: Human
<220> FEATURE:
<221> NAME/KEY: CDS
<222> LOCATION: (106)...(552)
<221> NAME/KEY: variation
<222> LOCATION: (79)...(79)
<223> OTHER INFORMATION: A, C, G or T
<221> NAME/KEY: variation
<222> LOCATION: (88)...(88)
<223> OTHER INFORMATION: A, C, G or T

<400> SEQUENCE: 3
actaggtgga gcagtgtttc ttccgcagac tcaactgaga agtcagcctc tggggcaggc       60
accaggaatc tgccttttna gttctgtntc cggcaggctt tgagg atg aag gct gcg     117
                                                  Met Lys Ala Ala
                                                   1 ggc att ctg acc ctc att ggc tgc ctg gtc aca ggc gcc gag tcc aaa       165
Gly Ile Leu Thr Leu Ile Gly Cys Leu Val Thr Gly Ala Glu Ser Lys
 5                  10                  15                  20 atc tac act cgt tgc aaa ctg gca aaa ata ttc tcg agg gct ggc ctg       213
Ile Tyr Thr Arg Cys Lys Leu Ala Lys Ile Phe Ser Arg Ala Gly Leu
             25                  30                  35 gac aat tac tgg ggc ttc agc ctt gga aac tgg atc tgc atg gca tat       261
Asp Asn Tyr Trp Gly Phe Ser Leu Gly Asn Trp Ile Cys Met Ala Tyr
         40                  45                  50 tat gag agc ggc tac aac acc aca gcc cag acg gtc ctg gat gac ggc       309
Tyr Glu Ser Gly Tyr Asn Thr Thr Ala Gln Thr Val Leu Asp Asp Gly
     55                  60                  65 agc atc gac tac ggc atc ttc cag atc aac acg ttc gcg tgg tgc aga       357
Ser Ile Asp Tyr Gly Ile Phe Gln Ile Asn Thr Phe Ala Trp Cys Arg
 70                  75                  80 cgc gga aag ctg aag gag aac aac cac tgc cac gtc gcc tgc tca gcc       405
Arg Gly Lys Leu Lys Glu Asn Asn His Cys His Val Ala Cys Ser Ala
 85                  90                  95                 100 ttg atc act gat gac ctc aca gat gca att atc tgt gcc agg aaa att       453
Leu Ile Thr Asp Asp Leu Thr Asp Ala Ile Ile Cys Ala Arg Lys Ile
             105                 110                 115 gtt aaa gag aca caa gga atg aac tat tgg caa ggc tgg aag aaa cat       501
Val Lys Glu Thr Gln Gly Met Asn Tyr Trp Gln Gly Trp Lys Lys His
                 120                 125                 130 tgt gag ggc aga gac ctg tcc gag tgg aaa aaa ggc tgt gag gtt tcc       549
Cys Glu Gly Arg Asp Leu Ser Glu Trp Lys Lys Gly Cys Glu Val Ser
             135                 140                 145 taa actggaactg gacccaggat gctttgcagc aacgccctag gatttgcagt            602
 * gaatgtcc                                                              610

<210> SEQ ID NO 4
<211> LENGTH: 148
<212> TYPE: PRT
<213> ORGANISM: Human

<400> SEQUENCE: 4

Met Lys Ala Ala Gly Ile Leu Thr Leu Ile Gly Cys Leu Val Thr Gly
 1               5                  10                  15

Ala Glu Ser Lys Ile Tyr Thr Arg Cys Lys Leu Ala Lys Ile Phe Ser
```

-continued

```
                     20                  25                  30

Arg Ala Gly Leu Asp Asn Tyr Trp Gly Phe Ser Leu Gly Asn Trp Ile
            35                  40                  45

Cys Met Ala Tyr Tyr Glu Ser Gly Tyr Asn Thr Thr Ala Gln Thr Val
 50                  55                  60

Leu Asp Asp Gly Ser Ile Asp Tyr Gly Ile Phe Gln Ile Asn Thr Phe
 65                  70                  75                  80

Ala Trp Cys Arg Arg Gly Lys Leu Lys Glu Asn Asn His Cys His Val
                85                  90                  95

Ala Cys Ser Ala Leu Ile Thr Asp Asp Leu Thr Asp Ala Ile Ile Cys
                100                 105                 110

Ala Arg Lys Ile Val Lys Glu Thr Gln Gly Met Asn Tyr Trp Gln Gly
            115                 120                 125

Trp Lys Lys His Cys Glu Gly Arg Asp Leu Ser Glu Trp Lys Lys Gly
    130                 135                 140

Cys Glu Val Ser
145

<210> SEQ ID NO 5
<211> LENGTH: 29
<212> TYPE: DNA
<213> ORGANISM: Human
<220> FEATURE:
<223> OTHER INFORMATION: Oligonucleotide primer

<400> SEQUENCE: 5
ttccggatcc atgaaggctg cgggcattc                                    29

<210> SEQ ID NO 6
<211> LENGTH: 29
<212> TYPE: DNA
<213> ORGANISM: Human
<220> FEATURE:
<223> OTHER INFORMATION: Oligonucleotide primer

<400> SEQUENCE: 6
cttcgtcgac ttaggaaacc tcacagcct                                    29

<210> SEQ ID NO 7
<211> LENGTH: 29
<212> TYPE: DNA
<213> ORGANISM: Human
<220> FEATURE:
<223> OTHER INFORMATION: Oligonucleotide primer

<400> SEQUENCE: 7
ttccaagctt atgaaggctg cgggcattc                                    29

<210> SEQ ID NO 8
<211> LENGTH: 29
<212> TYPE: DNA
<213> ORGANISM: Human
<220> FEATURE:
<223> OTHER INFORMATION: Oligonucleotide primer

<400> SEQUENCE: 8
cttcggatcc ttaggaaacc tcacagcct                                    29

<210> SEQ ID NO 9
<211> LENGTH: 28
<212> TYPE: DNA
<213> ORGANISM: Human
```

```
<220> FEATURE:
<223> OTHER INFORMATION: Oligonucleotide primer

<400> SEQUENCE: 9
ttccaagctt aaaatctaca ctcgttgc                                              28

<210> SEQ ID NO 10
<211> LENGTH: 19
<212> TYPE: PRT
<213> ORGANISM: Human
<220> FEATURE:
<223> OTHER INFORMATION: Signature Sequence of lysozyme and
      alpha-lactoalbumin
<221> NAME/KEY: VARIANT
<222> LOCATION: (2)...(4)
<223> OTHER INFORMATION: Any amino acid
<221> NAME/KEY: VARIANT
<222> LOCATION: (6)...(7)
<223> OTHER INFORMATION: Any amino acid
<221> NAME/KEY: VARIANT
<222> LOCATION: (8)...(8)
<223> OTHER INFORMATION: Leucine, methionine or phenylalanine
<221> NAME/KEY: VARIANT
<222> LOCATION: (9)...(11)
<223> OTHER INFORMATION: Any amino acid
<221> NAME/KEY: VARIANT
<222> LOCATION: (12)...(12)
<223> OTHER INFORMATION: Aspartate, glutamate, or asparagine
<221> NAME/KEY: VARIANT
<222> LOCATION: (13)...(13)
<223> OTHER INFORMATION: Leucine or Isoleucine
<221> NAME/KEY: VARIANT
<222> LOCATION: (14)...(18)
<223> OTHER INFORMATION: Any amino acid

<400> SEQUENCE: 10

Cys Xaa Xaa Xaa Cys Xaa Xaa Xaa Xaa Xaa Xaa Xaa Xaa Xaa
 1               5                  10                  15

Xaa Xaa Cys

<210> SEQ ID NO 11
<211> LENGTH: 147
<212> TYPE: PRT
<213> ORGANISM: Ring-necked pheasant

<400> SEQUENCE: 11

Met Arg Ser Leu Leu Ile Leu Val Leu Cys Phe Leu Pro Leu Ala Ala
 1               5                  10                  15

Pro Gly Lys Val Tyr Gly Arg Cys Glu Leu Ala Ala Ala Met Lys Arg
                20                  25                  30

Met Gly Leu Asp Asn Tyr Arg Gly Tyr Ser Leu Gly Asn Trp Val Cys
            35                  40                  45

Ala Ala Lys Phe Glu Ser Asn Phe Asn Thr Gly Ala Thr Asn Arg Asn
        50                  55                  60

Thr Asp Gly Ser Thr Asp Tyr Gly Ile Leu Gln Ile Asn Ser Arg Trp
 65                 70                  75                  80

Trp Cys Asn Asp Gly Arg Thr Pro Gly Ser Lys Asn Leu Cys His Ile
                85                  90                  95

Pro Cys Ser Ala Leu Leu Ser Ser Asp Ile Thr Ala Ser Val Asn Cys
            100                 105                 110

Ala Lys Lys Ile Val Ser Asp Gly Asn Gly Met Asn Ala Trp Val Ala
        115                 120                 125

Trp Arg Lys His Cys Lys Gly Thr Asp Val Asn Val Trp Ile Arg Gly
    130                 135                 140
```

-continued

```
Cys Arg Leu
145

<210> SEQ ID NO 12
<211> LENGTH: 146
<212> TYPE: PRT
<213> ORGANISM: Red Guenon

<400> SEQUENCE: 12

Met Lys Ala Val Ile Ile Leu Gly Leu Val Leu Ser Val Thr Val
1               5                   10                  15

Gln Gly Lys Ile Phe Glu Arg Cys Glu Leu Ala Arg Thr Leu Lys Arg
                20                  25                  30

Leu Gly Leu Asp Gly Tyr Arg Gly Ile Ser Leu Ala Asn Trp Val Cys
            35                  40                  45

Leu Ala Lys Trp Glu Ser Gly Tyr Asn Thr Gln Ala Thr Asn Tyr Asn
        50                  55                  60

Pro Gly Asp Gln Ser Thr Asp Tyr Gly Ile Phe Gln Ile Asn Ser His
65                  70                  75                  80

Tyr Trp Cys Asn Asn Gly Lys Thr Pro Gly Ala Val Asn Ala Cys His
                85                  90                  95

Cys Asn Ala Leu Leu Gln Asp Asn Ile Ala Asp Ala Val Thr Cys Ala
                100                 105                 110

Lys Arg Val Val Arg Asp Pro Gln Gly Ile Arg Ala Trp Val Ala Trp
            115                 120                 125

Arg Asn His Cys Gln Asn Arg Asp Val Ser Gln Tyr Val Gln Gly Cys
        130                 135                 140

Gly Val
145
```